US006410706B1

(12) United States Patent
Pai et al.

(10) Patent No.: US 6,410,706 B1
(45) Date of Patent: Jun. 25, 2002

(54) NUCLEIC ACID ENCODING CHITIN-BINDING RECEPTOR KINASE

(75) Inventors: Hyun-Sook Pai; Jang-Ryol Liu; Hye-Sun Cho; Youn-Sung Kim, all of Taejon-si (KR)

(73) Assignee: Korea Research Institute of Bioscience and Biotechnology (KR)

( * ) Notice: Subject to any disclaimer, the term of this patent is extended or adjusted under 35 U.S.C. 154(b) by 0 days.

(21) Appl. No.: 09/503,922

(22) Filed: Feb. 14, 2000

(30) Foreign Application Priority Data

Feb. 12, 1999 (KR) .............................. 99-4938

(51) Int. Cl.[7] .......................... C12N 15/52; C12N 5/10; C12N 15/63
(52) U.S. Cl. .................... 536/23.2; 435/69.1; 435/71.1; 435/71.2; 435/183; 435/194; 435/325; 435/252.33; 435/254.11; 435/320.1; 435/471
(58) Field of Search .............................. 536/23.1, 23.2; 435/69.1, 71.1, 71.2, 194, 252.3, 254.11, 252.33, 471, 183

(56) References Cited

PUBLICATIONS

Wang et al., The PR5K receptor protein kinase from *Arabidopsis thaliana* is structurally related to a family of plant defense proteins, Plant Biology, Proc. Natl. Acad. Sci, USA vol. 93, pp. 2598–2602 (1996).

Ito et al., Identification of a high–affinity binding protein for N–acetylchitooligosaccharide elicitor in the plasma membrane of suspension–cultured rice cells by affinity labeling, The Plant Journal, 1997 12(2), 347–356.

Song et al., A Receptor Kinase–Like Protein Encoded by the Rice Disease Resistance Gene, Xa21, Science, vol. 270, Dec. 1995, pp. 1804–1806.

*Primary Examiner*—Prema Mertz
(74) *Attorney, Agent, or Firm*—Roberts & Mercanti LLP.

(57) ABSTRACT

The present invention provides a novel receptor kinase and the gene thereof which can be used for activating plant defense systems against several pathogens such as fungi. The receptor kinase CHRK1 of this present invention has an extracellular domain similar to a chitinase, and whose gene expression is stimulated by infection of TMV. In addition, the receptor kinase CHRK1 contains a chitin-binding activity as well as a kinase activity so that it binds to chitin of fungal cell wall as a chitin receptor, stimulates a kinase domain, and thus effectively activates versatile plant defense systems. Therefore, the receptor kinase CHRK1 of this present invention can be used for developing plants having high resistance to fungi.

9 Claims, 6 Drawing Sheets

NUCLEIC ACID ENCODING CHITIN-BINDING RECEPTOR KINASE

FILED OF THE INVENTION

The present invention relates to a novel chitin-binding receptor kinase and the gene thereof encoding the receptor kinase isolated from tobacco.

Particulary, the present invention relates to a receptor kinase having a specific binding activity to oligomers or polymers of chitin molecules and its gene derived from *Nicotiana tabacum*.

The said receptor kinase has an extracellular domain homologous to other chitinases which are chitin-degrading enzymes, and its gene expression is specifically induced by infection of tobacco mosaic virus(TMV) and fungal pathogen. The receptor kinase and its gene in the present invention is regarded as a chitin signal transduction receptor localized in the cell membrane which activates plant defense systems, and thus makes plants operate the defense systems to various kinds of pathogens.

BACKGROUND OF THE INVENTION

Following the invasion of a plant by a potential pathogen, the pathogen either successfully proliferates in the host, causing associated disease symptoms, or its growth is halted by the defenses of the host plant. One such defense is the hypersensitive response (HR), a rapid cellular necrosis near the site of the infection that correlates with generation of activated oxygen species, production of antimicrobial compounds and reinforcement of host cell walls. Other defenses include systemic acquired resistance (SAR), which effectively protects the plant against subsequent attack by a broad range of pathogens.

A number of plant disease resistance genes activated by signal molecules of pathogens have been cloned, and similar features have been discovered among many of these resistance genes, in spite of the diversity of pathogens against which they act. These features include a leucine-rich-repeat (hereinafter, referred to as 'LRR'), a motif found in a multitude of eukaryotic proteins with roles in signal transduction(Kobe and Deisenhofer, *Trends Biochem. Sci.*, 9, 415–421, 1994). The LRR motif is thought to be involved in protein-protein interactions and may allow interaction with other proteins that are involved in plant disease resistance. In addition, nucleotide binding sites and leucine zippers are shared among many resistance genes(Dangl, *Cell*, 80, 383–386, 1995; Staskawicz et al., *Science*, 268, 661–667, 1995). These motifs are presented and similarly organized among resistance gene products from plants as diverse as tobacco, tomato, rice, flax, and Arabidopsis, suggesting a common mechanism underlying disease resistance signal transduction throughout the plant kingdom.

Recently, it is known that the plant receptor kinase is a factor of signal transduction of plant defense. It is revealed that many kinds of receptor kinases in plants are involved in hormone reactions, organ developments, and interactions between plants and pathogens. Several kinds of R(resistance) gene of plants which show resistance to specific types of pathogens have been identified as receptor kinase genes. (Wang, X. et al., *Proc. Natl. Acad. Sci.*, 93, 2598–2602, 1998).

The plant receptor kinase is classified into several groups based on the amino acid sequence of the extracellular domain. However, a receptor kinase which contains a chitinase-like domain has not been reported.

It is well known that chitinase activity increases dramatically after pathogen invasion and this is presumably due to the host plant's attempts to degrade the chitin of the fungal cell wall. Chitin is an important elicitor activating the plant defense system to increase the level of reactive oxygen species(ROS), synthesize phytoalexins, and stimulate transcriptions of several genes of defense proteins. Hitherto, the general transduction mechanism of chitin has not been reported, but several evidences that the signal transduction is initiated by recognition between receptor and the elicitor have been reported. In addition, chitinase has been shown in vitro to inhibit fungal and insect growth, and in transgenic plants a bacterial chitinase has been shown to exhibit inhibitory effects towards numerous pathogens and pests including insects.

Until now, many researchers have attempted to develop plants having a resistance to fungi by activating defense systems that plants originally own. Actually, overexpression of chitinases or glucanases in infected plants as defense proteins have been observed. At the gene level, it is revealed that a species-specific resistance gene from *Zea maize* (corn), Hm1 confers resistance against specific races of the fungal pathogen *Cochliobolus carbonum* by controlling degradation of a fungal toxin(Johal and Briggs, *Science*, 258:985–987, 1992).

However, development of resistant plants using the defense systems has failed, and even a successful example has not reached the practical stage because of its petty effects. It shows that it is impossible to obtain enough resistance for practical use by expression of one or two plant defense proteins.

Therefore, in order to obtain plants having a high resistance to pathogens, it must be considered to use whole plant defense systems corresponding to infection of pathogens. The most prominent strategy for obtaining resistant plants is to make plants recognize rapidly the infectious signal of pathogens and activate more effective defense systems. For the purpose of obtaining plants highly resistant to many kinds of fungi, isolation of the receptor kinase genes involved in signal transduction related to plant defense systems has been required.

In order to develop pathogen-resistant plants with activated defense systems, these inventors have investigated and purified a novel receptor kinase containing the extracellular domain similar to chitinase derived from *Nicotiana tabacum*.

Thus, these inventors have demonstrated that this novel receptor kinase may represent a receptor protein of plant defense systems regulating chitin signal transduction, of which chitinase domain binds to chitins in an extracellular space and activates the kinase domain in a cytoplasm.

SUMMARY OF THE INVENTION

It is an object of this invention to provide a novel receptor kinase CHRK1 and the gene thereof for developing pathogen-resistant plants.

In accordance with the present invention, the foregoing objects and advantages are readily obtained.

The present invention provides the novel receptor kinase which contains chitinase related sequence and has a binding activity to chitins.

Particularly, this invention provides a receptor kinase CHRK1 derived from *Nicotiana tabacum* described by amino acid sequence of SEQ ID NO: 1.

In addition, this invention provides the cDNA sequence of receptor kinase described by nucleotide sequence of SEQ ID NO: 2 derived from *Nicotiana tabacum*. The receptor kinase gene in the present invention can be detected in *Zea maize, Oryza sativa, Perunia inflata*, or *Brassica oleracea*.

This invention also provides the plasmid vector pCHRK1 comprising the receptor kinase cDNA (Accession NO: KCTC 0561BP).

Further objects and advantages of the present invention will appear hereinafter.

C-terminus: kinase domain;

TM: transmembrane domain.

Figure 2:
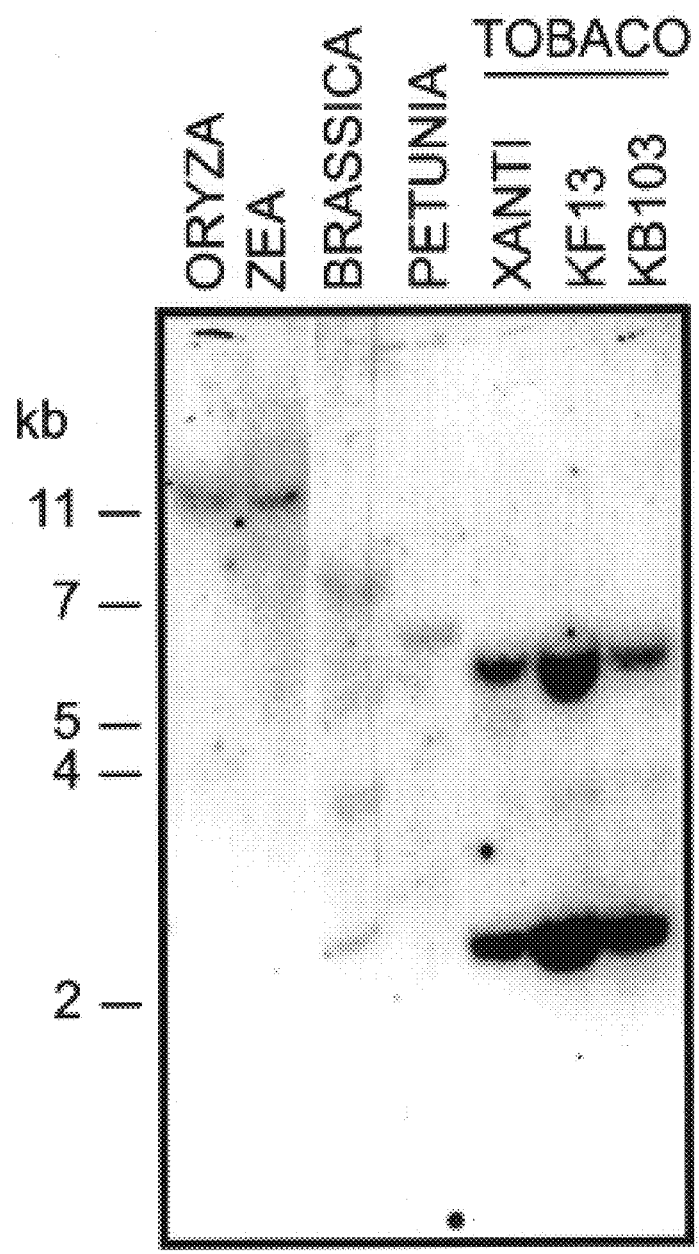

FIG. 2 shows the result of Southern blot analysis of genomic DNAs of several plants containing CHRK1 homologous gene.

Figure 3:
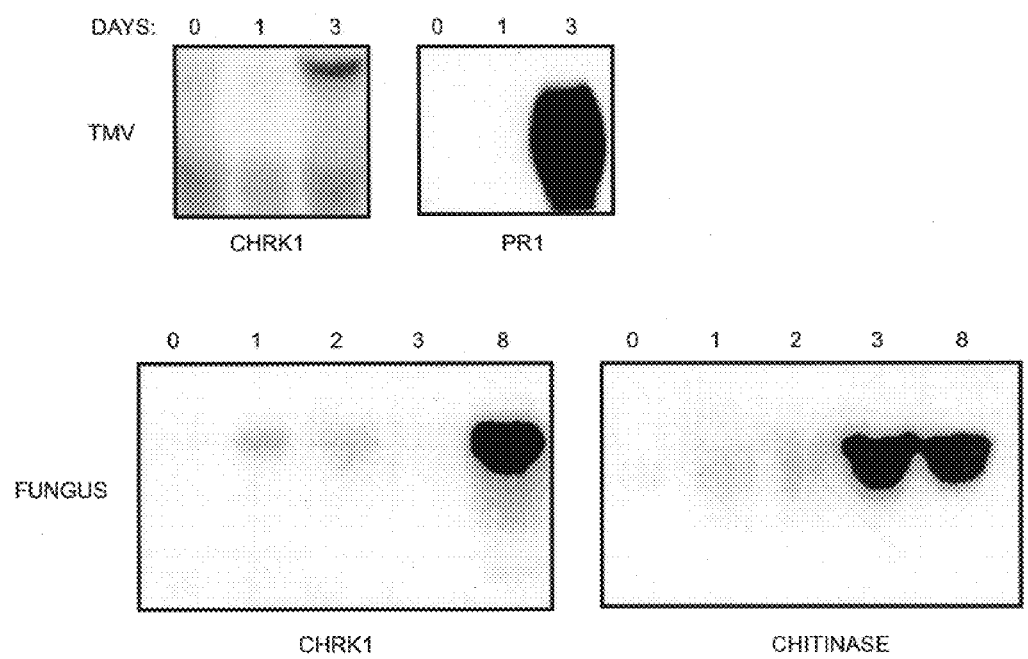

FIG. 3 shows increased mRNA level of the receptor kinase CHRK1 gene by infection of TMV and fungal pathogen(*phytophthora parasitica*) compared with other gene expression patterns responsible for resistance using PR1 and chitinase gene probes as controls.

Figure 4:
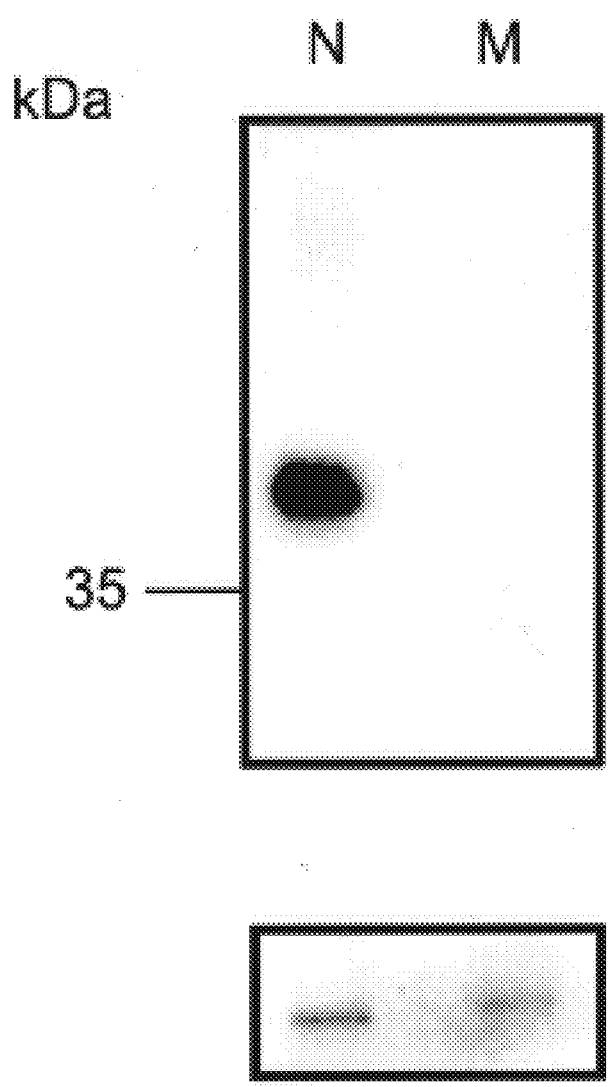

FIG. 4 shows result of autophosphorylation assay of the recombinant kinase domain of receptor kinase CHRK1 and mutant CHRK1 substituted from Lys of ATP binding residue to Asp.

Figure 5:
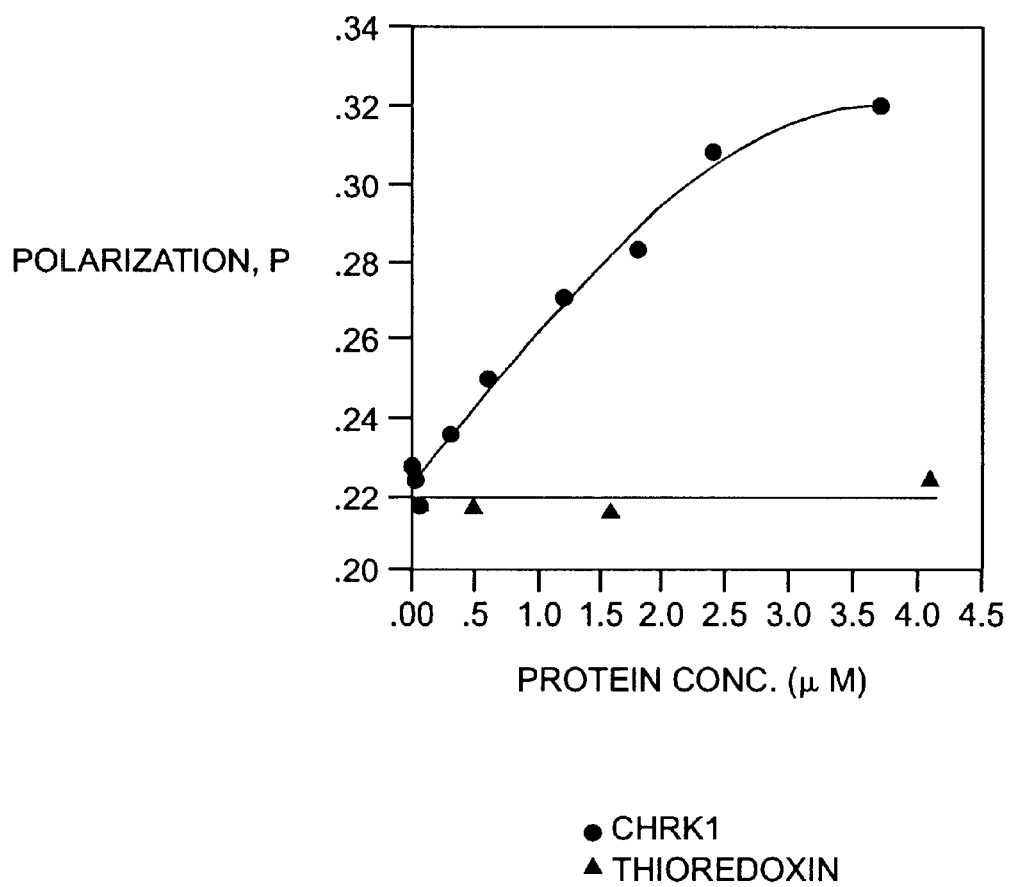

FIG. 5 shows result of fluorescence polarization analysis which determines binding activities between the receptor kinase CHRK1 and chitin molecules.

Figure 6:
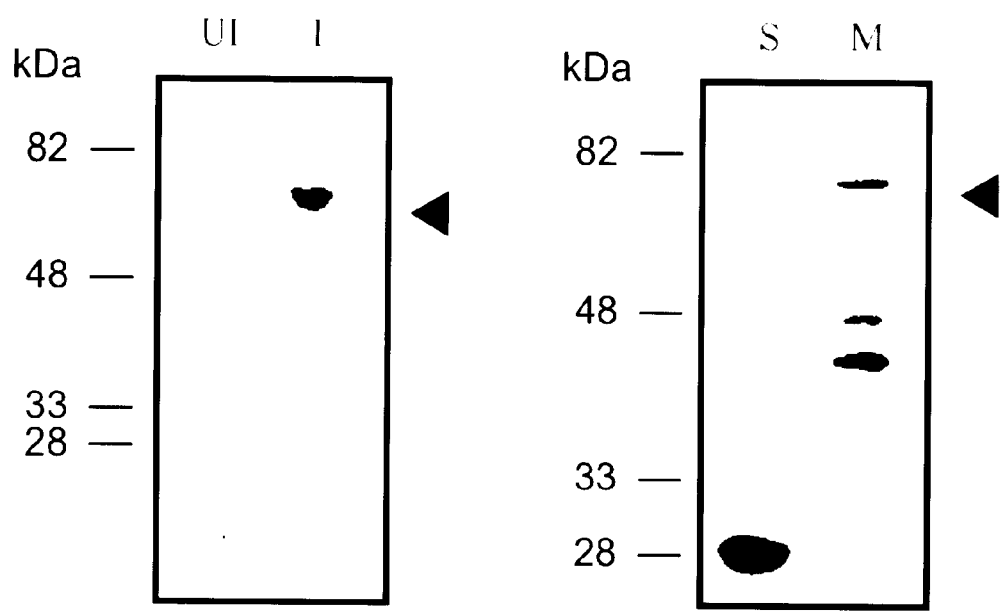

FIG. 6 shows expression patterns of proteins by Western blot analysis using polyclonal antibody against receptor kinase CHRK1, where UI: protein extracts from *E. coli* before induction;

I: protein extracts from *E. coli* after induction;

S: soluble proteins from tobacco leaves;

M: membrane proteins from tobacco leaves.

DETAILED DESCRIPTION OF THE INVENTION

The present invention provides a novel receptor kinase CHRK1 and the gene thereof which can be used for activating plant defense systems against several pathogens such as various fungi.

This invention provides a receptor kinase CHRK1 derived from *Nicotiana tabacum* described by amino acid sequence of SEQ ID NO: 1.

This invention provides the cDNA sequence of receptor kinase described by nucleotide sequence of SEQ ID NO: 2 derived from *Nicotiana tabacum*.

This invention also provides the plasmid vector pCHRK1 comprising the receptor kinase cDNA (Accession NO: KCTC 0561BP).

The receptor kinase and its gene in this invention will be utilized in developing resistant plants to fungal pathogen.

Hereinafter, the present invention is described in detail.

The present invention demonstrates that the novel receptor kinase derived from *Nicotiana tabacum* comprises an animo acid sequence similar to that of chitinase and has chitin-binding activity. Thus, the present invention verifies that this receptor kinase is the chitin receptor of plants capable of recognizing chitins of pathogens such as fungi.

Figure 1:
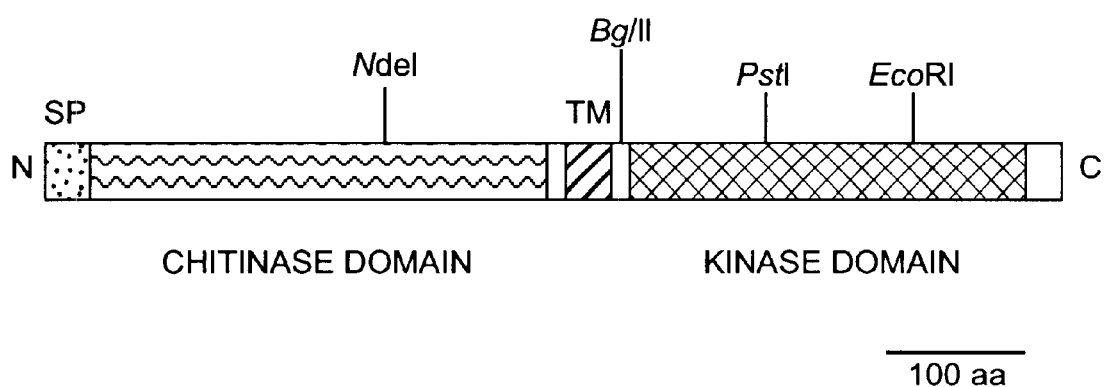
FIG. 1 shows the restriction map of a receptor kinase CHRK1 gene derived from *Nicotiana tabacum*, where N-terminus: chitinase domain.

The CHRK1 gene of this invention has a typical structure of receptor kinases, which consists of a signal peptide at the N-terminus, an extracellular domain very similar to a chitin-degrading enzyme chitinase, a transmembrane domain containing 23 amino acids and a kinase domain at the C-terminus(see FIG. 1).

The receptor kinase CHRK1 contains 739 amino acids which is described by SEQ ID NO: 1 and its cDNA is 2943 bp and the nucleotide sequence is described by SEQ ID NO: 2.

The chitinase domain of receptor kinase CHRK1 shows 41% homology with class V chitinase of tobacco, 23% homology with that of *Bacillus circulans* and 19% homology with that of *Serratia marcescens*. In addition, the kinase domain of CHRK1 also shows 47% homology with that of SRK6 receptor kinase from *Brassica oleracea*.

Especially the amino acid sequence of CHRK1 chitinase domain differs from that of other chitinases because Glu in Asp-Glu residues essential for chitinase activity is substituted to Val. It is expected that a mutation of Glu residue results in lose of chitinase activity of receptor kinase CHRK1, and in fact the recombinant chitinase domain expressed from *E. coli* lacks chitinase enzyme activity.

Besides CHRK1homologous sequences are also detected from *Zea maize, Oryza sativa, Petunia inflata*, or *Brassica oleracea*. Precisely, by genomic Southern analysis of the above mentioned plants, it is determined that the tobacco genome contains only one CHRK1 gene and other plants contain a CHRK1-homologous gene (see FIG. 2).

The receptor kinase CHRK1 differs in expression patterns based on regions of plant organs or whether the plant is infected or not. In detail, the different gene expression of receptor kinase CHRK1 is demonstrated by Northern blot analysis which shows that CHRK1 gene is expressed highly in flowers, lowly in leaves, and very little in roots and stems. Particularly in flowers, CHRK1 gene is poorly expressed at growing stages but highly expressed at flowering stages. mRNA accumulation of the CHRK1 gene in leaves is strongly stimulated by infection of TMV and fungus (see FIG. 3).

Autophosphorylation assay of the recombinant kinase domain of CHRK1 suggests that the above receptor kinase CHRK1 have a functional kinase activity. However, the mutant CHRK1 substituted from Lys of ATP binding residue to Asn does not show any kinase activity (see FIG. 4).

The chitinase activity and the chitin-binding activity of receptor kinase CHRK1 in this invention are analysed using its recombinant chitinase domain. Consequently, the recombinant chitinase domain has a chitin-binding activity and lacks a chitinase activity. By fluorescence polarization and competition analysis using Mu-chitotriose and Mu-chitotrose conjugated to fluorophor, it is determined that the recombinant protein exhibits a specific binding activity to chitooligosaccharides because of its chitin-binding activity (see FIG. 5). However, it does not show any chitinase activity for oligomeric as well as polymeric chitin as a substrate.

The chitinase active domain of receptor kinase CHRK1 is analyzed by using polyclonal antibody recognizing chitinase domain specifically. In detail, soluble and membrane proteins were purified from tobacco leaves, and analyzed by Western blot using above CHRK1 polyclonal antibody. As a result, the receptor kinase CHRK1 detected from membrane proteins has a molecular weight of 75 KDa (see FIG. 6).

As described above, an extracellular domain of receptor kinase CHRK1 has a chitin-binding activity, and a N-terminal kinase domain has a kinase activity. The receptor kinase CHRK1 interacts with chitin of fungal cell wall by exposed chitinase domain in cell exterior as a chitin receptor to activate a kinase domain, and thus transfers fungal infectious signal into cell interior to activate versatile defense systems. At this time, expected plant defense systems contain strengthening of cell wall through lignin synthesis, accumulation of phytoalexins, synthesis of reactive oxygen species, and gene expression of proteinase inhibitor, chitinase, or glucanase and so forth.

The present invention is further illustrated with reference to the following examples that are not intended to be in any way limiting to the scope of the invention as claimed.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Isolation of the Receptor Kinase CHRK1 Gene from Tobacco cDNA Library

In order to isolate cDNA of receptor kinase CHRK1, 210 bp DNA fragment containing kinase sequence was obtained by PCR from flower RNA using primers whose sequence is conserved in eukaryotic kinase. Using above kinase DNA fragment as a probe, CHRK1 cDNA was isolated from tobacco cDNA library by plaque hybridization assay. The CHRK1 cDNA cloned into λ ZAP II vector (Stratagene) was converted into pBluescript vector (Stratagene) through in vivo excision. The nucleotide sequence of the identified cDNA is described in SEQ ID NO: 2. As a result of analyzing the CHRK1 cDNA by PC-GENE program, it was demonstrated that receptor kinase CHRK1 had a specific receptor kinase structure, consisting of a chitinase-like amino acid sequence in an extracellular domain, a kinase domain in a cytoplasm, and a transmembrane region in between them (FIG. 1).

The recombinant pBluescript plasmid containing the receptor kinase cDNA was cloned into a pbluescript vector and was designated pCHRK1. E. coli transformant of the plasmid vector pCHRK1 was deposited in Korean Collection for Type Cultures (KCTC) of Korean Research Institute of Bioscience and Biotechnology (KRIBB) on Dec. 5, 1998 (Accession NO: KCTC 0561BP).

Example 2

Investigation of Homologous Genes of the Receptor Kinase CHRK1 in Other Plant Species For the purpose of investigation of homologous genes of the receptor kinase CHRK1 in various plants, these inventors purified genomic DNAs from *Zea maize, Oryza sativa, Petunia inflata, Brassica oleracea* and 3 cultivars of tobacco (Xanti, KF113, KB103), respectively. 10 ug of the genomic DNA were digested with restriction enzymes EcoR I, EcoR V, and Hind III. After enzyme reactions, the DNAs were electrophoresed in a 0.8% agarose gel, and blotted to a nylon membrane in 0.4 N NaOH. The probe was a random-labeled 800 bp EcoR I/Xho I cDNA fragment of CHRK1. Hybridization was carried out in 5×SSC, 0.05×blotto (Sambrook, J. et al., Molecular Cloning, A Laboratory Manual, Ed2. Cold Springs Harbor Laboratory Press, Cold Springs Harbor, N.Y., 1989) at 60° C. for 16 hours. The blot was washed twice for 30 minutes each in 0.2 ×SSC, 0.1% SDS at 60° C. As a result, it was demonstrated that the CHRK1 homologous gene exists in *Zea maize, Oryza sativa, Petunia inflata,* and *Brassica oleracea* (FIG. 2).

Example 3

Measurement of the Kinase Activity of a Kinase Domain in the Receptor Kinase CHRK1

To estimate the kinase activity of receptor kinase CHRK1, these inventors expressed fusion proteins in which thioredoxin was conjugated to a kinase domain of the receptor kinase CHRK1. Then, these fusion proteins were separated by Ni column (Novagen), and thioredoxin was removed by using enterokinase. 1 ug of the obtained kinase domain was phosphorylated in 20 ul of a phosphorylation buffer(25 mM HEPES, pH 7.5, 1 mM DTT, 10 mM $MgCl_2$ 10 mM $MnCl_2$, 10 uCi [$\gamma$-$^{32}$p] ATP) for 1 h at 37° C.

It was demonstrated that the 35 KDa kinase domain region was phosphorylated by SDS-polyacrylamide gel electrophoresis(SDS-PAGE). On the other hand, the mutant form which was substituted from Lys in ATP binding amino acid residue to Asn did not show any kinase activity (FIG. 4). Consequently, the result demonstrated that the kinase domain of receptor kinase CHRK1 in this invention possesses functional kinase activity.

Example 4

Chitin Binding Activity of a Chitinase Domain in the Receptor Kinase CHRK1

In order to examine the chitinase activity of receptor kinase CLRK1, the recombinant chitinase domain corresponding to amino acid residues 1 to 359 of SEQ. ID NO: 1 was purified from E. coli, and its chitinase activity was estimated by fluorescence polarization assay. Particularly, it was observed that the chitinase domain was covalently bound to fluorophor conjugated chitin oligomer Mu-chitotriose and Mu-chitotetrose, by its increased polarization value(excitation 318 nm: emission 373 nm). However, the polarization of thioredoxin used as a control did not increase at all (see FIG. 5).

As a result of Scratchard plot analysis, dissociation constant (kd) value of MU-chitotriose was estimated to be 800 nM. In case of using MU-chitotriose or MU-chitotetrose probe without fluorophor as a competitor, binding activity between the chitinase domain and MU-chitotriose or MU-chitotetrose conjugated with fluorophor was inhibited by the competitor. Consequently, the initial polarization value was decreased. It shows the receptor kinase CHRK1 is specifically bound to chitin oligomers.

Example 5

Distribution of the Receptor Kinase CHRK1 in Cell

To examine distribution sites of the receptor kinase CHRK1 in cell, the recombinant chitinase domain of SEQ ID NO: 1 expressed in *E. coli* was purified and injected into rabbit to produce polyclonal antibody. Before use, the antibody was purified using protein-A agarose bead and a sepharose column linked with *E. coli* total proteins.

As a result of Western blot analysis using this polyclonal antibody, it was demonstrated that this CHRK1 polyclonal antibody recognized only the recombinant CHRK1 chitinase from *E. coli* total proteins after induction (FIG. 6). In addition, by Western blot analysis using this CHRK1 polyclonal antibody with soluble membrane proteins extracted from tobacco, the membrane proteins smaller than 75 KDa of molecular weight were supposed to be excised forms of the receptor kinase CHRK1 by protease. The 25 KDa soluble protein recognized by above polyclonal antibody was considered to be a chitinase not related with the receptor kinase CHRK1.

EFFECT OF THE INVENTION

As described above, the receptor kinase CHRK1 of this present invention has an extracellular domain similar to chitinases, and whose gene expression is stimulated by infection of TMV and fungus. In addition, the receptor kinase CHRK1 contains a chitin-binding activity as well as a kinase activity. It is expected that CHRK1 binds to chitin of fungal cell wall as a chitin receptor, stimulates a kinase domain, and thus effectively activates versatile plant defense systems. Therefore, the receptor kinase CHRK1 of this present invention can be used for developing fungus-resistant plants.

What is claimed is:

1. An isolated nucleic acid encoding a receptor kinase having the amino acid sequence of SEQ ID NO:1, said nucleic acid comprising the nucleotide sequence of SEQ ID NO:2.

2. The isolated nucleic acid according to claim 1 wherein the nucleic acid is isolated from a plant selected from the group consisting of *Zea maize, Oryza saliva, Petunia inflata, Brassica oleracea* and *Nicotiana tabacum*.

3. A vector comprising the isolated nucleic acid according to claim 1.

4. A host cell which is transformed with the vector according to claim 3.

5. The vector according to claim 3 wherein the vector is a plasmid.

6. The vector according to claim 3, that is plasmid pCHRK1 deposited as KCTC 0561BP.

7. The host cell according to claim 4 wherein the host cell is an *Escherichia coli* cell.

8. The host cell according to claim 7, wherein the vector is pCHRK1.

9. An isolated nucleic acid encoding a receptor kinase having the amino acid sequence of SEQ ID NO: 1.

* * * * *

SEQUENCE LISTING

<160> NUMBER OF SEQ ID NOS: 2

<210> SEQ ID NO 1
<211> LENGTH: 739
<212> TYPE: PRT
<213> ORGANISM: Nicotiana tabacum

<400> SEQUENCE: 1

```
Met Ser Ser Lys Asn Leu Phe Ser Phe Leu Phe Leu Leu Val Leu Pro
 1               5                  10                  15

Phe Ser Ser Ser Asp Ala Thr Ala Trp Ile Lys Ser Gly Phe Trp
            20                  25                  30

Tyr Ala Gly Ser Glu Phe Pro Val Pro Glu Ile Pro Ser Thr Met Phe
        35                  40                  45

Thr His Ile His Phe Ala Phe Ala Tyr Ile Asn Ala Ser Ser Phe Glu
    50                  55                  60

Leu Tyr Val Ser His Ser Asp Glu Pro Tyr Ile Ser Thr Phe Ser Asn
65                  70                  75                  80

Thr Val Lys Gln Lys Asn Pro Ser Val Ile Thr Leu Leu Ser Ile Trp
                85                  90                  95

Gly Gly Arg Asp Glu Ser Pro Asn Phe Phe Ala Met Thr Ser Gln Phe
            100                 105                 110

Ser Arg Arg Lys Ser Phe Ile Thr Thr Ser Ile Lys Thr Ala Arg Gln
        115                 120                 125

Tyr Gly Phe Gln Gly Leu Asp Leu Ile Gly Val Asn Pro Asn Thr Asp
    130                 135                 140

Ala Asn Met Thr Asn Met Arg Ser Phe Ile Glu Glu Trp Arg Thr Ala
145                 150                 155                 160

Ile Asn Ser Glu Ser Lys Ser Ser Gly Thr Arg Thr Leu Ile Leu Thr
                165                 170                 175

Met Gly Ala Tyr Tyr Ser Pro Met Leu Asp Ser Met Ser Tyr Pro Ile
            180                 185                 190

Asp Thr Ile Ile Arg Asn Phe Asp Trp Val His Leu Lys Ala Tyr Ala
        195                 200                 205

Ala Leu Tyr Asp Pro Thr Ser Lys Leu Asn Thr Asp Tyr Gly Ile Lys
    210                 215                 220

Glu Trp Ile Lys Arg Gly Leu Pro Ala Asn Lys Ile Val Leu Gly Leu
225                 230                 235                 240

Ala Tyr His Gly Tyr Ala Trp Thr Leu Val Asn Pro Lys His Asn Thr
                245                 250                 255

Val Arg Thr Pro Ala Arg Gly Leu Ala Ile Thr Gln Asp Gly Ser Ile
            260                 265                 270

Ser Tyr Arg Tyr Ile Lys Gln Tyr Met Lys Ser Tyr Gly Val Thr Pro
        275                 280                 285

Val Tyr Asn Ser Thr Phe Val Val Asn Tyr Val Thr Ile Gly Ser Phe
```

```
              290                 295                 300
Trp Ile Gly Tyr Asp Asp Val Glu Ala Ile A rg Thr Lys Val Ser Tyr
305                 310                 315                 320

Ala Lys Asp Lys Gly Leu Leu Gly Phe Ala la Phe Gln Ile Pro Ser
                325                 330                 335

Asp Asp Val Asn Trp Glu Leu Ser Lys Thr A la Gln Asp Glu Glu Glu
                340                 345                 350

Glu Asp Gln Ser Gly Ser Asn Arg Arg Leu L eu Ala Ile Leu Leu Pro
                355                 360                 365

Thr Leu Thr Leu Thr Ile Leu Leu Ser T hr Ile Val Phe Ile Leu
        370                 375                 380

Lys Lys Lys Thr Leu Arg Ser Glu Gly Ile A rg Glu Leu Asn Glu Arg
385                 390                 395                 400

Ala Ile Gly His Asn Leu Lys Val Phe Lys P he Asp Lys Ile Lys Ala
                405                 410                 415

Ala Thr Asp Asn Phe Ser Ile Lys Asn Lys L eu Gly Glu Gly Gly Phe
                420                 425                 430

Gly Pro Val Tyr Lys Gly Arg Leu Ser Asp G ly Gln Glu Ile Ala Ile
                435                 440                 445

Lys Arg Leu Ser Ala Tyr Ser Lys Gln Gly V al Glu Glu Phe Gln Asn
450                 455                 460

Glu Val Thr Leu Ala Ser Lys Leu Gln His V al Asn Val Leu Gln Leu
465                 470                 475                 480

Gln Gly Cys Cys Thr Glu Arg Glu Glu Lys I le Leu Ile Tyr Glu Tyr
                485                 490                 495

Met Pro Asn Lys Ser Leu Asp Phe Tyr Leu T yr Asp Pro Val Gln Ser
                500                 505                 510

Leu Gln Leu Asp Trp Glu Thr Arg Val Arg I le Ile Glu Gly Val Thr
        515                 520                 525

Gln Gly Leu Leu Tyr Leu Gln Glu Tyr Ser A la Phe Thr Val Ile His
                530                 535                 540

Arg Asp Leu Lys Ala Ser Asn Ile Leu Leu A sp Asp Glu Met Lys Pro
545                 550                 555                 560

Lys Ile Ser Asp Phe Gly Ile Ala Lys Leu P he Gln Lys Asp Glu Lys
                565                 570                 575

Glu Ala Asn Thr Gly Arg Ile Val Gly Thr T yr Gly Cys Val Pro Pro
                580                 585                 590

Glu Tyr Val Lys Arg Gly Leu Tyr Ser Arg L ys Tyr Asp Val Tyr Ser
                595                 600                 605

Phe Gly Val Leu Leu Gln Ile Leu Gly G lu Lys Lys Asn Ser Ser
        610                 615                 620

Glu Tyr Gly Ile Lys Asn Asp Leu Asn Leu L eu Glu Tyr Ala Tyr Glu
625                 630                 635                 640

Leu Trp Glu Lys Gly Asn Gly Val Asp Phe L eu Asp Leu Ser Leu Gln
                645                 650                 655

Asp Asp Ser Arg Ile Gly Lys Gln Leu Arg T yr Met Gln Ala Ala Leu
                660                 665                 670

Leu Cys Val Gln Glu Lys Trp Glu Asp Arg P ro Ser Met Leu Glu Val
                675                 680                 685

Tyr Ser Met Leu Lys Asn Glu Thr Glu Val L eu Pro Asn Pro Lys Val
        690                 695                 700

Pro Ala Phe Ser Lys Asn Lys Asp Asn Asp T hr Gln Glu Thr Leu Val
705                 710                 715                 720
```

```
Thr Pro Asp Leu Thr Cys Ser Asp Asn Ser Leu Thr Ile Ser Gln Leu
            725                 730                 735

Ile Ala Arg

<210> SEQ ID NO 2
<211> LENGTH: 2943
<212> TYPE: DNA
<213> ORGANISM: Nicotiana tabacum

<400> SEQUENCE: 2
gaattcggca cgagaatcat ttttgatcac aaaggaacaa gcatacaaca a attgaccaa     60 ttcaatcttt acaagcaaag gggttaggca aatcaaaaac ttagttatag a cctttacat    120 attgtgttac atggcacttc ttttggttat gacggtggtg tatagccagt t tgggcgtac    180 ctcgactatt ctcaccagca catacacttt atcaagaata cctgttatcg t gttacaagg    240 cactttacca agaagtttac aaggttgaca gttagatatg tcctgctggt t ctaaaagag    300 tattgcttga catcaagaat ctttgctaaa gaagaattta actgtttatt t caaatgtct    360 tccaaaaacc tcttctcctt cctctttcta cttgttcttc cgttttcgag t tcttctgat    420 gcaacagctt ggataaaatc tgggttctgg tatgctggca gtgagtttcc a gttcctgaa    480 attccttcta ctatgttcac acacattcac tttgcctttg catatattaa c gcttcaagt    540 tttgagcttt acgtatctca ctcagatgaa ccgtatatct ctaccttctc a acactgtg     600 aagcaaaaga atccctcagt tatcacactt ctatccatcg gggaggaag a gatgagtcc    660 cctaattttt tcgcgatgac tagccagttt tctcgtagga aatctttcat c acaacgtca    720 ataaaaactg ctcgacaata tggatttcaa gggctggatc ttattggtgt c aacccgaac    780 acagatgcaa acatgactaa tatgagatca ttcattgaag agtggcggac a gcgattaat    840 tctgagtcca agagttctgg tacaagaaca ctgatcttga ctatgggagc a tactactca    900 cctatgctag attctatgtc ctacccaata gatacaatta tcagaaactt t gattgggtt    960 catctcaaag catatgcagc tttatatgac cctactagca aactaaatac a gactatggt   1020 ataaaggaat ggatcaagag aggattacca gccaataaaa tagttctagg t ttggcatac   1080 catggttatg catggacact tgtgaatcca aaacataaca cggtacgcac a cctgcaaga   1140 ggtttggcaa taacacaaga cggatcaatt agctacagat acatcaagca g tatatgaaa   1200 agttatggag tcacaccagt ctataattcc acatttgttg tgaactatgt c accattgga   1260 tcattttgga ttggttatga tgatgtcgag gctattagaa ctaaagtttc t tatgcgaag   1320 gataaggggc ttcttggttt tgctgcattc caaataccaa gtgatgatgt c aattgggag   1380 ctgtcaaaaa cagctcagga cgaagaagaa gaagatcaaa gcggcagcaa c cgaaggtta   1440 ctggcaattc ttctgccaac gctcacccctc accattctcc tactaagtac a atagtgttt   1500 atcttgaaaa agaaaacctt aagatctgaa gggatcaggg aattgaatga a agagctata   1560 ggtcataacc taaagttttt caatttgac aaaataaaag cagctacaga c aatttctcc   1620 attaaaaaca agctgggaga aggaggattt ggacctgttt ataagggaag g ttaagtgat   1680 gggcaagaaa ttgcaataaa acggctttca gcatactcta agcaaggagt a gaagagttc   1740 cagaatgagg tcacacttgc ttcaaagtta cagcatgtca atgttctaca a cttcaggga   1800 tgttgcactg aaagagaaga gaagatactg atttatgagt acatgccaaa t aaaagtttg   1860 gatttctacc tttacgatcc agtacagagc ctgcagttag attgggagac g cgggttcgt   1920 attatagaag gagttactca aggacttcta tacctacaag agtactcagc a ttcacagtc   1980
```

-continued

```
attcacagag acttgaaagc tagcaacatt ttactggacg atgagatgaa a ccgaaaatc   2040 tcagattttg gtatagctaa acttttccag aaagatgaaa aggaagcaaa c accggaagg   2100 attgtcggga cctatggttg tgttcctcca gagtacgtta agcgaggtct a tactccagg   2160 aaatatgacg tttacagttt tggagtttta ttgttgcaaa tccttggcga a aagaagaat   2220 tcaagtgaat atggaatcaa gaacgatctg aatcttctag aatatgcata t gaactttgg   2280 gaaaaaggca atggagtgga ttttcttgat ctgtcactgc aagatgattc t cgaataggc   2340 aagcaactga gatacatgca agctgcacta ttgtgtgtcc aagaaaaatg g gaagaccga   2400 ccatcgatgt tggaggtgta ctccatgctc aaaaatgaaa ctgaggtctt g cccaatcct   2460 aaagttcctg cctttccaa gaataaagac aatgacacac aagagacttt a gtcacacct   2520 gaccttactt gttcggataa tagtctcact atatcccaac ttatagccgt t aacacttca   2580 aagtttcagg gagcatttta atctcacaaa tggtcttttt gcctctgttt c tttacttgg   2640 tctccggaat cccgtagagc aagttactgt cgtatacaat acatcaccca g tcacaatta   2700 gcaacttttt aaataatttt ccttggttga aggaaaattg tttaagtagt g aattgaagt   2760 atgactaaag tagagtctaa catgtgatag cctatcaagg aaattccac a agttaacaa   2820 gttagatgcc aagcccggtc ttcttaaatt aattgatcca gcaacgacac t aaaacattg   2880 ccacagactg aagtatactc aatgattaac aaagatcatt ttcaaaaaaa a aaaaaaaa   2940 aaa                                                                 2943
```